United States Patent [19]

Boger et al.

[11] 4,098,902

[45] Jul. 4, 1978

[54] 1-PHENYL-1,3,5,7-TETRAAZA-4-SULPHA-HEPT-1-EN-6-ONE DERIVATIVES

[75] Inventors: Manfred Böger, Weil am Rhein, Germany; Jozef Drabek, Allschwil, Switzerland

[73] Assignee: Ciba-Geigy Corporation, Ardsley, N.Y.

[21] Appl. No.: 707,149

[22] Filed: Jul. 20, 1976

[30] Foreign Application Priority Data

Jul. 24, 1975 [CH] Switzerland .................... 9674/75
Feb. 17, 1976 [CH] Switzerland .................... 1909/76
Jun. 3, 1976 [CH] Switzerland .................... 7020/76

[51] Int. Cl.² .................... C07D 295/18; A01N 9/12; C07D 127/19
[52] U.S. Cl. .................... 424/322; 424/246; 424/248.5; 424/267; 424/274; 424/298; 260/453 RW; 260/553 A; 542/416
[58] Field of Search .......... 260/551 S, 240 G, 453 R, 260/453 RW, 553 A; 424/246, 248 S, 267, 274, 298, 315, 322

[56] References Cited

U.S. PATENT DOCUMENTS

| | | | |
|---|---|---|---|
| 3,853,966 | 12/1974 | Brown et al. | 260/545 R |
| 3,857,883 | 12/1974 | Cleveland | 260/545 R |
| 3,947,591 | 3/1976 | Rizzo et al. | 424/326 |

Primary Examiner—Henry R. Jiles
Assistant Examiner—R. W. Ramsuer
Attorney, Agent, or Firm—Harry Falber

[57] ABSTRACT

Compounds of the formula

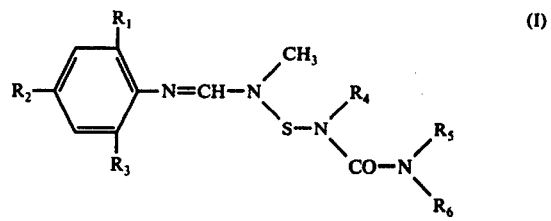

(I)

wherein $R_1$, $R_2$ and $R_3$ independently of one another are hydrogen, halogen, methyl or ethyl, $R_4$ is $C_1$-$C_8$-alkyl, $C_3$-$C_6$-cycloalkyl or ($C_3$-$C_6$-cycloalkyl)-methyl, and either (i) $R_5$ is hydrogen, $C_1$-$C_8$-alkyl, $C_1$-$C_4$-alkoxy, $C_3$-$C_6$-cycloalkyl or ($C_3$-$C_6$-cycloalkyl)-methyl, while $R_6$ is $C_1$-$C_8$-alkyl, $C_1$-$C_4$-alkoxy, $C_3$-$C_6$-cycloalkyl or ($C_3$-$C_6$-cycloalkyl)-methyl, or (ii) $R_5$ and $R_6$ together with the nitrogen atom to which they are attached represent a 5- or 6-membered heterocyclic ring optionally substituted by one or more $C_1$-$C_4$-alkyl groups and optionally including an oxygen or sulphur atom within the ring system, possess valuable insecticidal and in particular acaricidal properties.

28 Claims, No Drawings

1-PHENYL-1,3,5,7-TETRAAZA-4-SULPHA-HEPT-1-EN-6-ONE DERIVATIVES

The present invention provides new 1-phenyl-1,3,5,7-tetraaza-4-sulpha-hept-1-en-6-one derivatives which possess pesticidal activity, a process for obtaining them, pesticidal compositions which contain these derivatives as active principle, and a method of combating pests, which comprises the use of said derivatives.

The invention provides in particular the 1-phenyl-1,3,5,7-tetraaza-4-sulpha-hept-1-en-6-one derivatives of the formula I

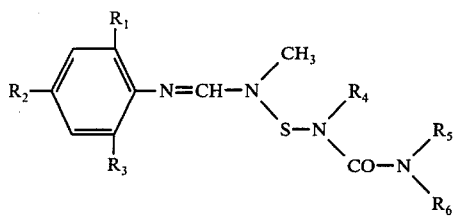 (I)

wherein $R_1$, $R_2$ and $R_3$ independently of one another represent a hydrogen or halogen atom or a methyl or ethyl group, $R_4$ represents a $C_1$-$C_8$-alkyl, $C_3$-$C_6$-cycloalkyl or ($C_3$-$C_6$-cycloalkyl)-methyl group, and either (i) $R_5$ represents a hydrogen atom or a $C_1$-$C_8$-alkyl, $C_1$-$C_4$-alkoxy, $C_3$-$C_6$-cycloalkyl or ($C_3$-$C_6$-cycloalkyl)-methyl group, while $R_6$ represents a $C_1$-$C_8$-alkyl, $C_1$-$C_4$-alkoxy, $C_3$-$C_6$-cycloalkyl or ($C_3$-$C_6$-cycloalkyl)-methyl group, or (ii) $R_5$ and $R_6$ together with the nitrogen atom to which they are attached represent a 5- or 6-membered heterocyclic ring optionally substituted by one or more $C_1$-$C_4$-alkyl groups and optionally including an oxygen or sulphur atom within the ring system.

Alkyl and alkoxy groups in formula I can be branched or straight-chain. Suitable examples of such groups are: methyl, methoxy, ethyl, ethoxy, n- and isopropyl or -propoxy, n-, iso-, sec.- and tert.-butyl or -butoxy, n-pentyl, n-hexyl, n-heptyl and n-octyl and isomers thereof. By cycloalkyl group is meant the cyclopropyl, cyclobutyl, cyclopentyl and cyclohexyl group, chiefly the cyclopropyl and cyclohexyl group. Such cycloalkyl groups also form the alkyl moiety of cycloalkyl-methyl substituents.

Heterocyclic groups represented by [-N($R_5$)($R_6$)] include the pyrrolidinyl, piperidinyl, morpholinyl and thiomorpholinyl group and the derivatives thereof which are mono- or disubstituted by alkyl of 1 to 4 carbon atoms, in particular by methyl, for example the 3-methylpyrrolidinyl, 3,4-dimethylpyrrolidinyl, 3-methylpiperidinyl, 4-methylpiperidinyl, 3,5-dimethylmorpholinyl and 3,5-dimethylthiomorpholinyl group.

Particularly preferred compounds on account of their action on pests, especially on insects and above all representatives of the order Acarina, are the compounds of the formula I, wherein $R_1$ represents a methyl or ethyl group, $R_2$ represents a hydrogen atom and $R_3$ represents a methyl or ethyl group, and those of the formula I wherein $R_1$ represents a methyl group, $R_2$ represents a halogen atom, in particular a chlorine atom, or a methyl group, and $R_3$ represents a hydrogen atom.

A particularly pronounced acaricidal action is exhibited by those compounds of the formula I, wherein $R_1$ represents a methyl group, $R_2$ represents a chlorine atom or a methyl group, $R_3$ represents a hydrogen atom, $R_4$ represents a $C_1$-$C_8$-alkyl, cyclopropyl, cyclohexyl or cyclopropylmethane group, in particular a $C_1$-$C_4$-alkyl group and above all a methyl group, and either (i) $R_5$ represents a hydrogen atom or a $C_1$-$C_8$-alkyl, methoxy, cyclohexyl or cyclopropyl group, in particular a hydrogen atom or a $C_1$-$C_4$-alkyl, methoxy or cyclohexyl group, while $R_6$ represents a $C_1$-$C_8$ alkyl group, in particular a $C_1$-$C_4$-alkyl group, or (ii) $R_5$ and $R_6$ together with the nitrogen atom to which they are attached form a pyrrolidinyl, morpholinyl or 3,5-dimethylmorpholinyl group.

The compounds of the formula I of the present invention are obtained by methods which are known per se, for example by reacting a formamidine of the formula II

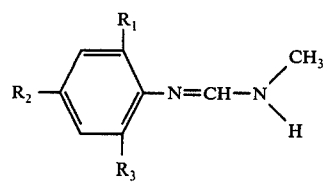 (II)

in the presence of a base, with a compound of the formula III

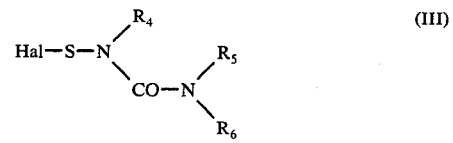 (III)

in which formulae $R_1$ to $R_6$ have the meanings previously assigned to them in formula I and Hal repesents a halogen atom, in particular a chlorine or bromine atom.

The process is carried out at a reaction temperature between $-20°$ C and $+30°$ C, at normal or elevated pressure, and preferably in a solvent or diluent which is inert to the reactants or in an excess of the base used. Solvents or diluents which are suitable for this reaction are for example: ethers and ethereal compounds, such as diethyl ether, dipropyl ether, dioxan, dimethoxyethane and tetrahydrofurane; amides, such as N,N-dialkylated carboxamides; aliphatic aromatic and halogenated hydrocarbons, in particular benzene, toluene, xylenes, chloroform and chlorobenzene; nitriles, such as acetonitrile; dimethyl sulphoxide and ketones, such as acetone and methyl ethyl ketone.

Suitable bases are tertiary amines, such as triethylamine, dimethyl aniline, pyridine, picoline and lutidine, hydroxides, oxides, carbonates and bicarbonates of alkali metals and alkaline earth metals, for example potassium tert. butylate and sodium methylate.

The derivatives of the formulae II and III used as starting materials are known (cf. for example U.S. Pat. No. 3,857,883; E. Kuhle, "Synthesis", 11 573 (1970); and British Pat. Nos. 964,640 and 1,340,600), or they can be obtained by known methods.

The compounds of the formula I have a broad biocidal action and can be used for combating a variety of plant and animal pests, for example as acaricides, insecticides, ectoparasiticides, plant regulators or herbicides.

They are suitable above all for combating acarides, for example ticks and mites of the families: Ixodidae, Argasidae, Tetranychidae and Dermanysidae.

The compounds of the formula I also have a notably good action on insects that are harmful to plants and animals and they can be used for combating e.g. insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelisae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae, and Pulicidae, and above all for combating aphids (*Aphis fabae*) and paddy stem borers (for example *Chilo suppressalis*). The compounds of the formula I are therefore particularly suitable for combating insects that damage fruit, vegetables, rice and ornamental plants.

The insecticidal or acaricidal action can be substantially broadened and adapted to prevailing circumstances by the addition of other insecticides and/or acaricides. Examples of suitable additives are: organic phosphorus compounds, nitrophenols and derivatives thereof, formamidines, ureas, pyethroids, carbamates, and chlorinated hydrocarbons.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, stickers, thickeners, binders and/or fertilizers.

For application, the compounds of the formula I may be processed to dusts, emulsion concentrates, granules, dispersions, sprays, to solutions or suspensions, in the conventional formulation which is commonly employed in application technology. Cattle dips and spray races, in which aqueous preparations are used, may also be mentioned.

The compositions according to the invention are manufactured in known manner by intimately mixing and/or grinding active substances of the formula I with the suitable carriers, with or without the addition of dispersants or solvents which are inert to the active substances.

The active substances may take, and be used in, the following forms:
Solid forms:
Dusts, tracking agents, granules, coated granules, impregnated granules and homogeneous granules.
Liquid forms:
(a) active substance concentrates which are dispersible in water: wettable powders, pastes, emulsions;
(b) solutions.

The content of active substance in the above described compositions is between 0.1% and 95%, in which connection it must be mentioned that higher concentrations can also be used if the compositions are applied from an aircraft or other appropriate application devices.

The active substances of the formula I can, for example, be formulated as follows:

Dusts

The following substances are used to obtain (a) a 5% and (b) a 2% dust:

(a)

5 parts of active substance,
95 parts of talcum;

(b)

2 parts of active substance,
1 part of highly disperse silicic acid,
97 parts of talcum.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3 - 0.8 mm).

The active substance is mixed with epichlorohydrin and dissolved with 6 parts of acetone; the polyethylene glycol and cetyl polyglycol ether are then added. The resultant solution is prayed on kaolin, and the acetone is subsequently evaporated in vacuo.

Wettable powder

The following constituents are used for the preparation of (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid.

(b)

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselgur,
46 parts of kaolin.

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in appropriate mills and rollers to yield wettable powders, which can be diluted with water to give suspensions of the desired concentration.

Emulsifiable concentrate

The following substances are used to produce a 10% emulsifiable concentrate:

(a)

10 parts of active substance,
3.4 parts of epoxidised vegetable oil,
3.4 parts of a combination emulsifier consisting of fatty alcohol polyglycol ether and alkyl aryl sulphonate calcium salt,
40 parts of dimethylformamide,
43.2 parts of xylene.

By diluting such a concentrate with water it is possible to manufacture emulsions of the desired concentration.

Spray

The following constituents are used to prepare (a) a 5% and (b) a 95% spray:

(a)

5 parts of active substance,
1 part of epichlorohydrin,
94 parts of benzene (boiling limits 160° C–190° C.

(b)

95 parts of active substance,
5 parts of epichlorohydrin.

The following Examples illustrate the invention in more detail.

EXAMPLE 1

Preparation of 1-(2-methyl-4-chlorophenyl)-3,5,7-trimethyl-1,3,5,7-tetraaza-4-sulpha-oct-1-en-6-one (compound 1)

To a solution of 18.3 g of N-methyl-N'-(4-chloro-2-methyl-phenyl)-formamidine in 200 ml of tetrahydrofurane are added 10.5 g of triethylamine. Thereafter 16.9 g of trimethylurea sulphenyl chloride are added dropwise with constant stirring and while cooling with an ice bath.

The reaction mixture is stirred for a further 1/2 hour at room temperature. The triethylamine hydrochloride is filtered off and the filtrate is concentrated and finally dried under a high vacuum, to yield the compound of the formula

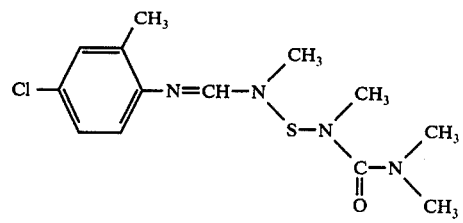

as a yellow oil with a refractive index of 1.5820 (20° C).
The following compounds of the formula Ia

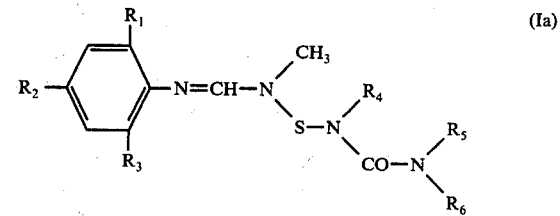

40 were obtained in analogous manner:

| Compound | $R_1$ | $R_2$ | $R_3$ | $R_4$ | $R_5$ | $R_6$ | Physical Data | |
|---|---|---|---|---|---|---|---|---|
| 2 | $CH_3$ | Cl | H | $CH_3$ | $CH_3O$ | $CH_3$ | $n_D^{20}$ | 1.5780 |
| 3 | $CH_3$ | Cl | H | $CH_3$ | $nC_4H_9$ | $CH_3$ | $n_D^{20}$ | 1.5638 |
| 4 | $CH_3$ | Cl | H | $CH_3$ | $-CH_2-CH_2-O-CH_2-CH_2-$ | | m.p. | 104–106° C |
| 5 | $CH_3$ | Cl | H | $CH_3$ | $-CH_2-CH_2-CH_2-CH_2-$ | | m.p. | 118–119° C |
| 6 | $CH_3$ | Cl | H | $CH_3$ | ⟨cyclohexyl-H⟩ | $CH_3$ | m.p. | 73–75° C |
| 7 | $CH_3$ | Cl | H | $nC_8H_{17}$ | $CH_3$ | $CH_3$ | $n_D^{20}$ | 1.5400 |
| 8 | $CH_3$ | $CH_3$ | H | $CH_3$ | $CH_3$ | $CH_3$ | $n_D^{20}$ | 1.5670 |
| 9 | $CH_3$ | $CH_3$ | H | $CH_3$ | $CH_3O$ | $CH_3$ | $n_D^{20}$ | 1.5634 |
| 10 | $CH_3$ | $CH_3$ | H | $CH_3$ | $nC_4H_9$ | $CH_3$ | $n_D^{20}$ | 1.5513 |
| 11 | $CH_3$ | $CH_3$ | H | $CH_3$ | $nC_3H_7$ | $nC_3H_7$ | $n_D^{20}$ | 1.5446 |
| 12 | $CH_3$ | $CH_3$ | H | $CH_3$ | $-CH_2-CH_2-O-CH_2-CH_2-$ | | m.p. | 82–84° C |
| 13 | $CH_3$ | $CH_3$ | H | $CH_3$ | $-CH_2-CH_2-CH_2-CH_2-$ | | m.p. | 82–83° C |
| 14 | $CH_3$ | $CH_3$ | H | ⟨cyclopropyl⟩ | $CH_3$ | $CH_3$ | m.p. | 73–75° C |
| 15 | $CH_3$ | Cl | H | $CH_3$ | $nC_3H_7$ | $nC_3H_7$ | $n_D^{20}$ | 1.5574 |
| 16 | $CH_3$ | Cl | H | ⟨cyclopropyl⟩ | $CH_3$ | $CH_3$ | m.p. | 101–103° C |
| 17 | $CH_3$ | Cl | H | $CH_3$ | H | $CH_3$ | m.p. | 80–83° C |
| 18 | $CH_3$ | Cl | H | $-CH_2-$⟨cyclopropyl⟩ | $CH_3$ | $CH_3$ | m.p. | 93–95° C |
| 19 | $CH_3$ | Cl | H | $CH_3$ | $-CH_2-$⟨cyclopropyl⟩ | $nC_3H_7$ | $n_D^{20}$ | 1.5641 |
| 20 | $CH_3$ | Cl | H | $CH_3$ | $nC_8H_{17}$ | $nC_8H_{17}$ | $n_D^{20}$ | 1.5266 |

-continued

| Compound | $R_1$ | $R_2$ | $R_3$ | $R_4$ | $R_5$ | $R_6$ | Physical Data | |
|---|---|---|---|---|---|---|---|---|
| 21 | $CH_3$ | Cl | H | $CH_3$ | \-$CH_2$-$\underset{CH_3}{CH}$-O-$\underset{CH_3}{CH}$-$CH_2$ | | $n_D^{20}$ | 1.5682 |
| 22 | $CH_3$ | Cl | H | cyclohexyl-H | $CH_3$ | $CH_3$ | $n_D^{20}$ | 1.5700 |
| 23 | $CH_3$ | $CH_3$ | H | $CH_3$ | cyclohexyl-H | $CH_3$ | m.p. | 95–97° C |
| 24 | $CH_3$ | $CH_3$ | H | $CH_3$ | \-$CH_2$-$\underset{CH_3}{CH}$-O-$\underset{CH_3}{CH}$-$CH_2$- | | m.p. | 78–79° C |
| 25 | $C_2H_5$ | H | $C_2H_5$ | $CH_3$ | $CH_3$ | $CH_3$ | $n_D^{20}$ | 1.5506 |
| 26 | $CH_3$ | $CH_3$ | H | $CH_3$ | H | $CH_3$ | | |
| 27 | $CH_3$ | $CH_3$ | H | -$CH_2$-cyclopropyl | $CH_3$ | $CH_3$ | m.p. | 71–73° C |
| 28 | $CH_3$ | $CH_3$ | H | $CH_3$ | -$CH_2$-cyclopropyl | $nC_3H_7$ | $n_D^{20}$ | 1.5529 |
| 29 | $CH_3$ | $CH_3$ | H | $CH_3$ | $nC_8H_{17}$ | $nC_8H_{17}$ | $n_D^{20}$ | 1.5198 |
| 30 | $CH_3$ | Br | H | -$CH_2$-cyclopropyl | $CH_3$ | $CH_3$ | m.p. | 98–100° C |
| 31 | $CH_2$ | Cl | H | $nC_4H_9$ | $CH_3$ | $CH_3$ | $n_D^{20}$ | 1.5580 |
| 32 | $CH_3$ | Cl | H | $nC_6H_{13}$ | $CH_3$ | $CH_3$ | $n_D^{20}$ | 1.5400 |

EXAMPLE 2

Action on *Chilo suppressalis*

Rice seedlings of the variety Caloro were reared in plastic pots (6 seedlings per pot) so that their roots became matted to a disc. The roots were immersed in a 0.08% solution of active substance and allowed to drip off. Each pot was then populated with 5 *Chilo suppressalis* larvae in the $L_2$ stage and the treated plants were subsequently replaced in the pots on top of the larvae. The percentage evaluation of mortality was made after 5 days.

In the above test, compounds of Example 1, especially compounds 1, 2, 5, 11, 14, 16 and 18 exhibited good action on *Chilo suppressalis*.

EXAMPLE 3

Action on *Aphis fabae* and *Myzus persicae*

Broad beans (*Vicia faba*) reared in pots were infested with the test insects (*Myzus persicae* and *Aphis fabae* respectively). Each plant was infested on average with 200 insects.

Twenty four hours after infestation, the test substance (0.1% aqueous emulsion obtained from a 10% emulsifiable concentrate) was applied to the leaves populated with the aphids using a pressure spray from a distance of 30 cm. Two plants were used per test substance. The test was carried out at a temperature of 24° C and 60% relative humidity.

In the above test, compounds of formula I acted positively on *Myzus Persicae* and *Aphis fabae*. Compounds 1, 8, 10 and 11 are to be singled out for their particularly good activity.

EXAMPLE 4

Action on ticks (A) *Rhipicephalus bursa*

Five adult ticks and 50 tick larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cotton-wool plug and placed on its head to enable the cotton wool to absorb the active substance emulsion.

The adults were evaluated after 2 weeks and the larvae after 2 days. Each test was repeated twice.

(B) *Boophilus microplus* (larvae)

Tests were carried out with 20 OP- sensitive and 20 OP-resistant larvae respectively using aqueous emulsions similar to those used in Test A. (The resistance refers to the tolerance towards diazinone).

The compounds of Example 1 acted in these tests on adults and larvae of *Rhipicephalus bursa* and OP-sensitive and OP-resistant larvae of *Boophilus microplus*. Compounds 3 and 11 are to be singled out on account of their particularly good activity.

EXAMPLE 5

Acaricidal action: *Tetranychus urticae* (OP-sensitive) and *T. cinnabarinus* (OP-tolerant)

The primary leaves of *Phaseolus vulgaris* plants were infected with an infested piece of leaf from a mass culture of the test species 16 hours before the test for acaricidal action. The treated plants were sprayed dripping wet with a test solution containing either 400 or 200 ppm of the test compound. Evaluation of the percentage mortality of the adults, larvae (all mobile stages) and eggs took place after 2 and 7 days.

As test species there were used:
(a) *Tetranychus urticae* (OP-sensitive) and
(b) *Tetranychus cinnabarinus*.

In the above test, the compounds of Example 1 acted well on both test species.

EXAMPLE 6

Acaricidal residual action: *Tetranychus urticae* ♀♀ (OP-resistant)

*Phaseolus vulgaris* plants in the 2-leaf stage were sprayed with a test solution containing 400 ppm of test substance until they were dripping wet and populated 48 hours later with adults (♀♀) of the species *Tetranychus urticae* (OP-resistant). Percentage evaluation of the mortality achieved took place after 5 days.

In the above test, 100% mortality was achieved with compounds 3, 4, 11, 13 and 23.

EXAMPLE 7

Acaricidal contact action on larvae: *Tetranychus urticae* (OP-resistant)

Adults (♀♀) of the species *Tetranychus urticae* were transferred to *Phaseolus vulgaris* plants in the two-leaf stage and left thereon for 24 hours of oviposition. The adults were removed and the larvae which had hatched out of the eggs were sprayed with a test solution containing 400 ppm of the test substance. Percentage evaluation of mortality was made after a further 5 days.

Compounds 2 to 4, 6, 8 to 11, 15 and 23 effected a 100% mortality in this test.

EXAMPLE 8

Acaricidal action: *Tetranychus urticae* (OP-resistant)

The test for ovicidal action was carried out in accordance with the larvicidal test described in Example 7, except that the test solution was sprayed on the 24 hour old eggs and the percentage mortality evaluated 6 days later (percentage of unhatched eggs).

The compounds of Example 1 exhibit a positive ovicidal action in this test. Compounds 1 to 4, 6, 10, 11, 13 and 23 are particularly suitable on account of their especially good activity.

We claim:

1. A compound of the formula

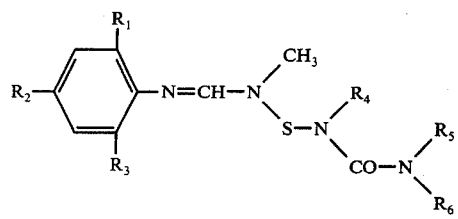

(I)

wherein
R$_1$, R$_2$ and R$_3$ independently of one another are hydrogen, halogen, methyl or ethyl,
R$_4$ is C$_1$-C$_8$-alkyl, C$_3$-C$_6$-cycloalkyl or (C$_3$-C$_6$-cycloalkyl)-methyl, and either
(i) R$_5$ is hydrogen, C$_1$-C$_8$-alkyl, C$_1$-C$_4$-alkoxy, C$_3$-C$_6$-cycloalkyl or (C$_3$-C$_6$-cycloalkyl)-methyl, while
R$_6$ is C$_1$-C$_8$-alkyl, C$_1$-C$_4$-alkoxy, C$_3$-C$_6$-cycloalkyl or (C$_3$-C$_6$-cycloalkyl)-methyl, or
(ii) R$_5$ and R$_6$ together with the nitrogen atom to which they are attached represent a 5- or 6- membered heterocyclic ring selected from the group consisting of pyrrolidinyl, piperidinyl, morpholinyl and thiomorpholinyl rings and the mono- and di-(C$_1$-C$_4$) alkyl derivatives thereof.

2. The compound according to claim 1 wherein
R$_1$ is methyl or ethyl,
R$_2$ is hydrogen and
R$_3$ is methyl or ethyl.

3. The compound according to claim 1 wherein
R$_1$ is methyl,
R$_2$ is halogen or methyl and
R$_3$ is hydrogen.

4. The compound according to claim 3 wherein
R$_1$ is methyl,
R$_2$ is chlorine or methyl,
R$_3$ is hydrogen
R$_4$ is C$_1$-C$_8$-alkyl, cyclopropyl, cyclohexyl or cyclopropylmethyl and either
(i) R$_5$ is hydrogen, C$_1$-C$_8$-alkyl, methoxy, cyclohexyl or cyclopropylmethyl, while
R$_6$ is C$_1$-C$_8$-alkyl or
(ii) R$_5$ and R$_6$ together with the nitrogen atom to which they are attached represent pyrrolidinyl, morpholinyl or 3,5-dimethylmorpholinyl.

5. The compound according to claim 4 wherein
R$_4$ is C$_1$-C$_4$-alkyl and either
(i) R$_5$ is hydrogen, C$_1$-C$_4$-alkyl, methoxy or cyclohexyl, while
R$_6$ is C$_1$-C$_4$-alkyl or
(ii) R$_5$ and R$_6$ together with the nitrogen atom to which they are attached represent pyrrolidinyl, morpholinyl or 3,5-dimethylmorpholinyl.

6. The compound according to claim 5 wherein R$_4$ is methyl.

7. The compound according to claim 6 of the formula

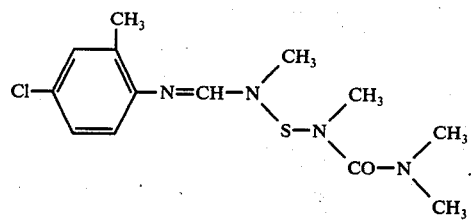

8. The compound according to claim 6 of the formula

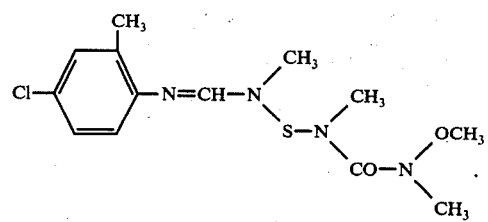

9. The compound according to claim 6 of the formula

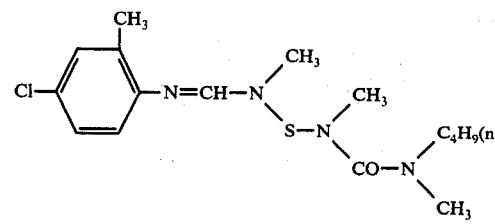

10. The compound according to claim 6 of the formula

11. The compound according to claim 6 of the formula

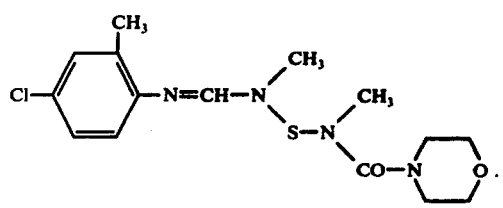

12. The compound according to claim 6 of the formula

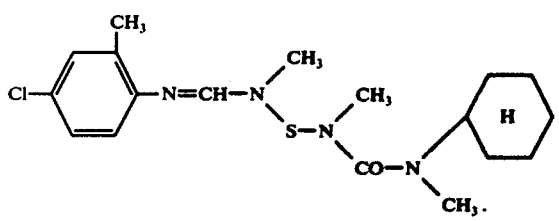

13. The compound according to claim 6 of the formula

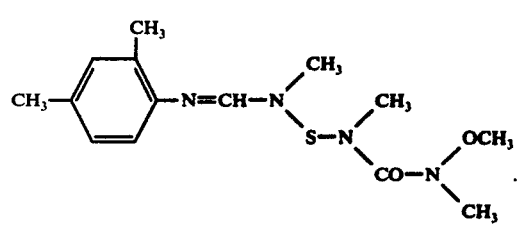

14. The compound according to claim 6 of the formula

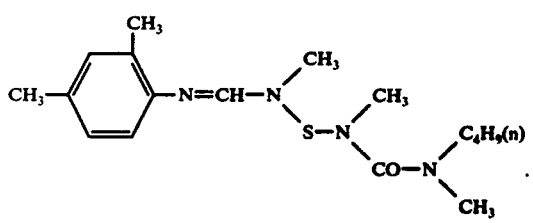

15. The compound according to claim 6 of the formula

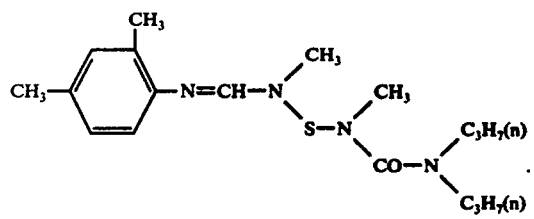

16. The compound according to claim 6 of the formula

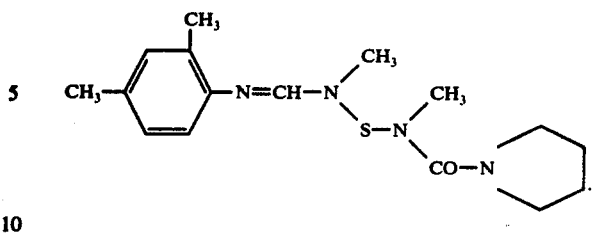

17. The compound according to claim 6 of the formula

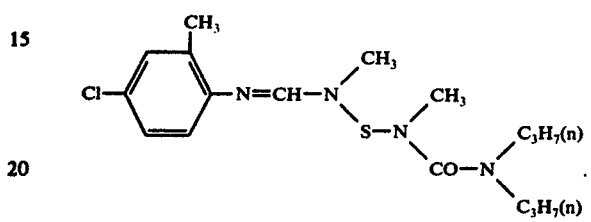

18. An insecticidal or acaricidal composition which comprises an insecticidally or acaricidally effective amount of a compound of the formula I as defined in claim 1 as active ingredient together with a suitable carrier therefor.

19. An insecticidal or acaricidal composition according to claim 18 wherein in the compound of the formula I
$R_1$ is methyl,
$R_2$ is chlorine or methyl and
$R_3$ is hydrogen.

20. An insecticidal or acaricidal composition according to claim 19 wherein in the compound of the formula I either
$R_1$, $R_4$ and $R_6$ are methyl,
$R_2$ is chlorine,
$R_3$ is hydrogen and
$R_5$ is n-butyl or
$R_1$, $R_2$ and $R_4$ are methyl,
$R_3$ is hydrogen and
$R_5$ and $R_6$ are n-propyl.

21. A method of combating pests of the class Insecta or of the order Acarina at a locus which comprises applying to said locus an insecticidally or acaricidally effective amount of a compound of the formula I as defined in claim 1.

22. A method according to claim 21 wherein the pests are of the order Acarina.

23. A method according to claim 22 wherein in the compound of the formula I
$R_1$ is methyl,
$R_2$ is chlorine or methyl and
$R_3$ is hydrogen.

24. A method according to claim 23 wherein in the compound of the formula I either
 $R_1$, $R_4$ and $R_6$ are methyl,
 $R_2$ is chlorine
 $R_3$ is hydrogen and
 $R_5$ is n-butyl or
 $R_1$, $R_2$ and $R_4$ are methyl,
 $R_3$ is hydrogen and
 $R_5$ and $R_6$ are n-propyl.

25. A method according to claim 24 wherein the locus comprises agricultural or horticultural crops or plants.

26. The compound according to claim 6 of the formula

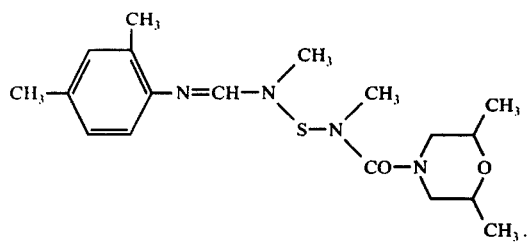

27. The compound according to claim 4 of the formula

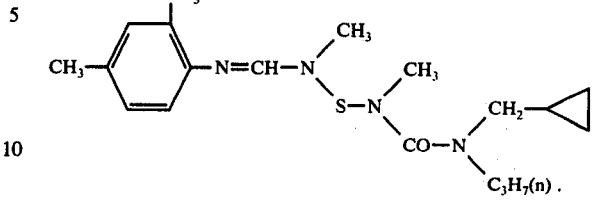

28. The compound according to claim 4 of the formula

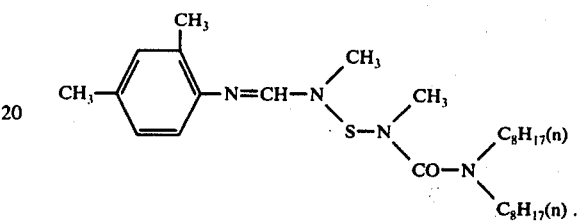

* * * * *